(12) United States Patent
Radley Young et al.

(10) Patent No.: US 7,520,865 B2
(45) Date of Patent: Apr. 21, 2009

(54) SURGICAL TOOL MECHANISM

(76) Inventors: Michael John Radley Young, Bremridge House, Bremridge, Ashburton, Newton Abbot, South Devon TQ13 7JX (GB); Stephen Michael Radley Young, Bremridge House, Bremridge, Ashburton, Newton Abbot, South Devon TQ13 7JX (GB)

( * ) Notice: Subject to any disclaimer, the term of this patent is extended or adjusted under 35 U.S.C. 154(b) by 329 days.

(21) Appl. No.: 10/509,258

(22) PCT Filed: Mar. 27, 2003

(86) PCT No.: PCT/GB03/01336

§ 371 (c)(1), (2), (4) Date: Apr. 6, 2005

(87) PCT Pub. No.: WO03/082133

PCT Pub. Date: Oct. 9, 2003

(65) Prior Publication Data

US 2005/0216045 A1 Sep. 29, 2005

(30) Foreign Application Priority Data

Mar. 28, 2002 (GB) .................... 0207318.7

(51) Int. Cl.
*A61H 7/00* (2006.01)
*A61B 18/18* (2006.01)
*A61B 17/32* (2006.01)

(52) U.S. Cl. .......... 601/133; 606/37; 606/169
(58) Field of Classification Search .......... 601/1, 601/2, 133; 606/169, 205; 269/86
See application file for complete search history.

(56) References Cited

U.S. PATENT DOCUMENTS

| 5,322,055 | A | 6/1994 | Davison et al. |
| 5,520,678 | A | 5/1996 | Heckele et al. |
| 5,669,544 | A * | 9/1997 | Schulze et al. .......... 227/176.1 |
| 5,873,873 | A | 2/1999 | Smith et al. |
| 6,773,409 | B2 * | 8/2004 | Truckai et al. ............. 606/27 |
| 6,984,220 | B2 * | 1/2006 | Wuchinich .................. 604/22 |

FOREIGN PATENT DOCUMENTS

WO WO 02/38057 A1 5/2002

* cited by examiner

*Primary Examiner*—Eric F Winakur
*Assistant Examiner*—Michael T Rozanski
(74) *Attorney, Agent, or Firm*—Carter, DeLuca, Farrell & Schmidt, LLP

(57) ABSTRACT

The surgical tool comprises a longitudinally extending waveguide (1) defining a longitudinal axis (2). A first jaw member (1b) is connected at a distal end of the waveguide (1). A longitudinally extending carrier tube (3) is rotatable about the waveguide (1) and a second jaw member (6) is pivotably mounted to a distal end of the carrier tube (3). An outer shroud (7) includes a guide lobe (9) bearing on a rearward face of the second jaw member. Rotation of the carrier tube (3) causes pivoting of the second jaw member (6) into and out of operative relationship with the first jaw member (1b).

29 Claims, 7 Drawing Sheets

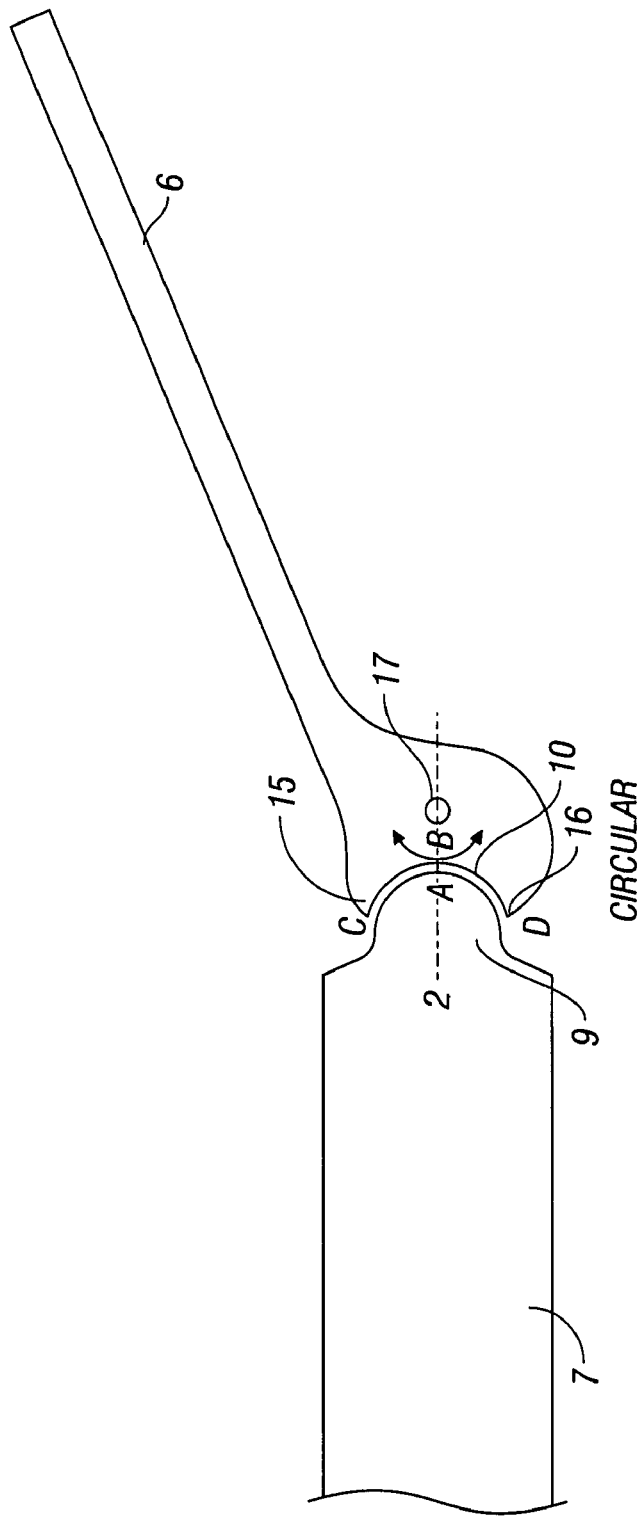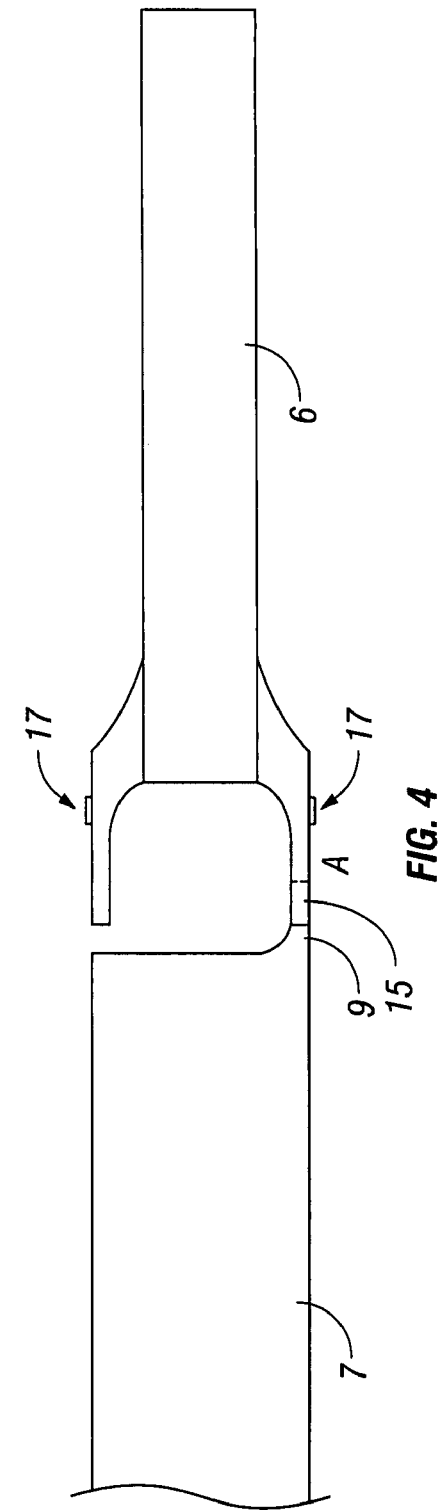

PARABOLIC

RECTANGULAR

SURGICAL TOOL MECHANISM

The present invention relates to a surgical tool, and to a mechanism for its operation. More particularly, but not exclusively, it relates to an improved mechanism for operating an ultrasonic cutting and coagulating tool.

The mechanism is applicable to any surgical tool, particularly a laparoscopic tool where the surgeon may use a scissors-type, a pistol or trigger type grip outside the body to operate a manipulative, gripping or clamping mechanism at a distal end of the tool within the body. It is particularly, but not exclusively, useful for use with ultrasonically operated haemostatic cutting tools.

The invention will be described herein, for convenience, with respect to a preferred use with a haemostatic cutting tool, but its use is not limited thereto.

Such haemostatic cutting tools are known from British Patent Number 2333709B, International Patent Applications Numbers PCT/GB99/00162 and PCT/GB00/01580, and U.S. Pat. No. 5,322,055.

Each of the above identified patents and patent applications describes a surgical tool comprising means to generate ultrasonic vibrations and a waveguide, operatively connected at a proximal end to said generating means, and provided at a distal end with cutting and/or coagulating means. Each tool is provided with a jaw to hold tissue to be treated in contact with the ultrasonically vibrating cutting and/or coagulating means.

While several different actuating mechanisms have been employed to operate said jaw, they all amount to a reciprocable actuating member pushing or pulling on a part of the jaw to move it about a pivot, the actuating member being controlled by manual movements of a user of the tool. This has been found not to give sufficiently precise and subtle control over the movement of the jaw. These mechanisms focus very much on being able to clamp tissue hard against the cutting and/or coagulating means, rather than achieving any delicacy in handling soft tissues.

In the applicant's UK Patent Application No. 0124923.4, a partial solution to the above problem is disclosed. Rotation of a tubular outer shroud surrounding the waveguide is employed to operate a jaw member pivotably mounted to a second tube, disposed within the outer shroud and around the waveguide. This allows improved control over the movement of the jaw.

However, the tool disclosed therein still has a number of shortcomings. Since the outer shroud is moveable, it cannot be affixed to the handset. The inner shroud is the one which is attached. Therefore the mechanism required within the handset of the tool, to convert a user's hand movements into rotational movements of the outer shroud, is relatively complex and requires very accurate machining to operate effectively.

The configuration of the tool and its assembly also makes it almost impossible, in practice, to separate the outer most shroud e.g. for cleaning, without extensive dismantling of the handset apparatus. Since this is the component most exposed to blood etc, it is a disadvantage that it cannot easily be separately cleaned.

A further problem, which has been encountered with all such laparoscopic tools with a jaw mechanism, is viewing the tissue to be treated while the tool is being operated. An endoscope is conventionally introduced alongside the laparoscopic tool, but it is frequently found that the pivoting jaw member of the tool obscures the operator's view of the tissue to be treated, during part or all of its pivoting movement. It is often difficult to reposition the endoscope at will in the confined spaces, in which such tools are used.

It is therefore an object of the present invention to provide a surgical tool, in particular an ultrasonic surgical tool comprising a jaw and an ultrasonically active cutting and/or coagulating means, wherein the motion of the jaw relative to the cutting and/or coagulating means may be accurately and precisely controlled by means of a mechanism which is straightforward to manufacture and permits easy separation of parts of the tool for cleaning.

It is further an object of the present invention to provide a surgical tool, and in particular an ultrasonic surgical tool, comprising a jaw mechanism, which obviates or eliminates the visibility problems described above.

According to the present invention, there is provided a surgical tool comprising a longitudinally extending guide means defining a longitudinal axis of said tool, a first jaw member at a distal end thereof, a longitudinally extending carrier means rotatable about said guide means, a second jaw member pivotably mounted to a distal end of said carrier means, and outer shroud means including operating means for said second jaw member whereby rotation of said carrier means acts on the operating means to cause pivoting of said second jaw member into and out of operative relationship with said first jaw member.

Preferably, the surgical tool is an ultrasonic surgical tool, and the elongate guide means is a waveguide, operatively connected at a proximal end to means to generate ultrasonic vibrations.

The first jaw member may then constitute ultrasonically vibratable cutting and/or coagulating means, and the second jaw member may be adapted to hold tissue to be treated against said cutting and/or coagulating means.

Advantageously, said carrier means is a carrier tube, comprising a tubular member concentrically surrounding said guide member.

The carrier tube may thus rotate within a tubular space defined by an inner wall of the outer shroud tube and an outer surface of the inner guide member.

The shroud means is preferably mounted non-rotatably to a handset of the tool.

Advantageously, the shroud means is detachably mounted to said handset.

Optionally, the carrier means is detachably mounted to the handset of the tool.

In a preferred embodiment, the operating means comprises a guide lobe extending forwardly from a distal end of the shroud means and disposed to bear on an opposing surface of the second jaw member.

Advantageously, the operating means comprises two cam lobes extending proximally towards the distal end of the guide means.

Optionally, a proximally facing surface of the second jaw member comprises an intermediate curved zone disposed between two protrusions, so disposed that the action of one said protrusion on the guide lobe of the operating areas acts to pivot the second jaw member into operative relationship with the first jaw member, and the action of the other said protrusion on the guide lobe acts to pivot the second jaw member away from said operative relationship.

The protrusions and the curved zone therebetween may cooperate with the guide lobe to move the second jaw member between open and closed dispositions by a rotational movement of the carrier means to which said jaw member is mounted of between 20 and 60 degrees, preferably between 25 and 45 degrees, optionally in the region of 30 degrees.

The curved zone may be so shaped that the second jaw member is caused to pivot comparatively slowly over a part of its travel and comparatively rapidly over another part of its travel.

The comparatively slow part of the travel of the second jaw member may define a coagulation step.

The comparatively rapid part of said travel may define a cutting step.

In an alternative embodiment, the operating means may be provided with more than one such guide lobe, preferably an odd number thereof.

In this case, the second jaw member may require only a single protrusion, guided by two said lobes and a curved interlobal zone therebetween.

Preferably the carrier means is operatively connected to a manually operatable control means.

The control means may include means to ensure substantially continuous contact between the guide lobe or lobes and the proximal face of the second jaw member, whatever the rotational disposition.

The carrier means may be biased in a proximal direction by a resilient biasing means, such as a spring means or a member of resilient material.

Alternatively, the control means may comprise cam means adapted to urge the carrier means in a proximal direction, optionally to an extent dependent on the rotational disposition of the carrier means.

Advantageously, said manually operable control means comprises a trigger type mechanism or a scissors-like mechanism.

Such a trigger-type mechanism may be so mounted pivotably to a housing that it engages in a part helical slot of a turning means integral with or operatively associated with said carrier means, whereby longitudinal movement of the trigger means causes rotation of the turning means and thereby of the carrier means.

Preferably, the cutting and/or coagulating means has a profile adapted to cut, separate and/or coagulate tissue, as appropriate to the purpose of the tool, and the second jaw member comprises a surface facing said cutting and/or coagulating means which has a complementary shape thereto.

In a preferred embodiment, the means to generate ultrasonic vibrations is adapted to generate torsional mode ultrasonic vibrations.

Alternatively, the means to generate ultrasonic vibrations is adapted to generate longitudinal mode ultrasonic vibrations.

According to a second aspect of the present invention, there is provided a surgical tool comprising a longitudinally extending first guide member having a first jaw member at a distal end thereof, a second jaw member movable into and out of operative relationship with the first jaw member and carrier means and operating means for the second jaw member so adapted that the second jaw member follows a three dimensional path when so moved.

Preferably, the movement of the second jaw member comprises substantially simultaneous pivoting movement about a first axis and rotation of said first axis about a second axis substantially orthogonal thereto.

Said second axis is advantageously parallel to or coincident with a longitudinal axis of the tool.

Said surgical tool may be an ultrasonic surgical tool.

The longitudinally extending first member may then be a waveguide for ultrasonic vibrations, optionally torsional mode ultrasonic vibrations, or alternatively longitudinal mode ultrasonic vibrations.

In a preferred embodiment, the tool is a surgical tool as described in the first aspect of the present invention.

Embodiments of the present invention will now be more particularly described by way of example, and with reference to the accompanying drawings, in which:

FIG. 3 is an elevation of the jaw mechanism of the tool of FIG. 1;

FIG. 4 is a plan view of the jaw mechanism of FIG. 3;

Figure 1:
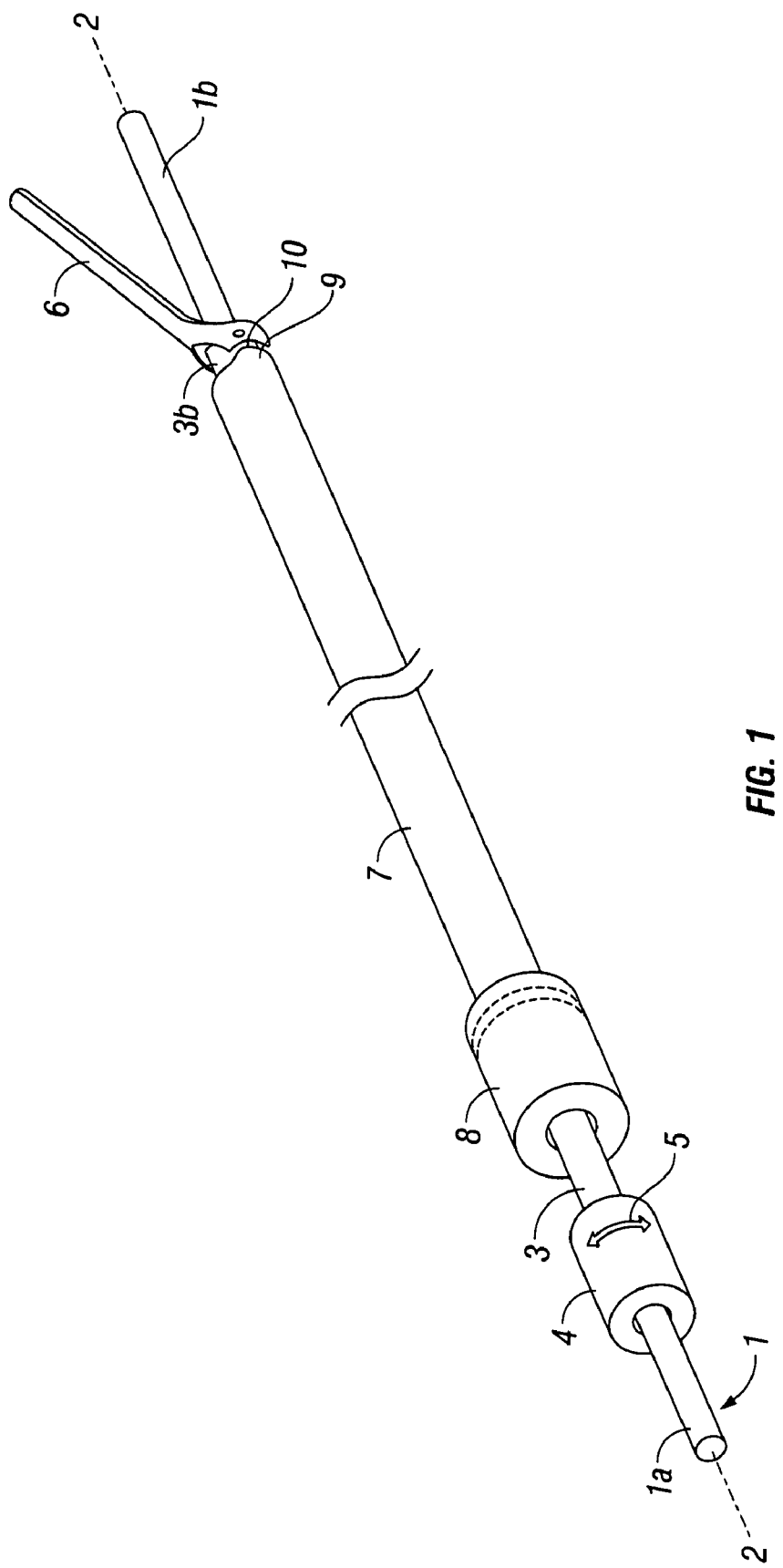
FIG. 1 is a schematic perspective view of a tool embodying the invention, with its handset and ultrasonic generator omitted.
Figure 8:
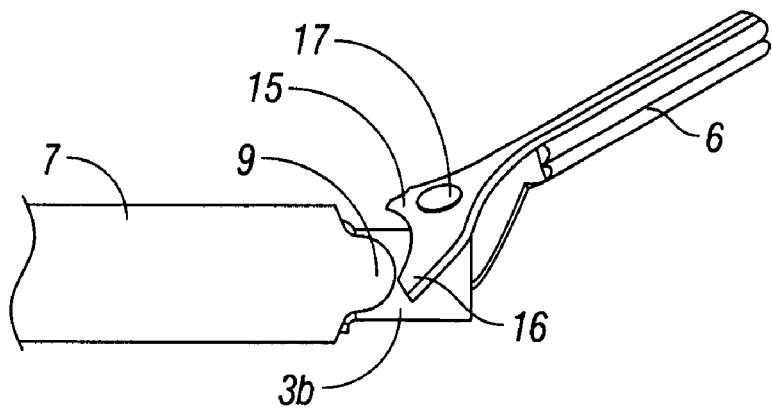
Figure 9:
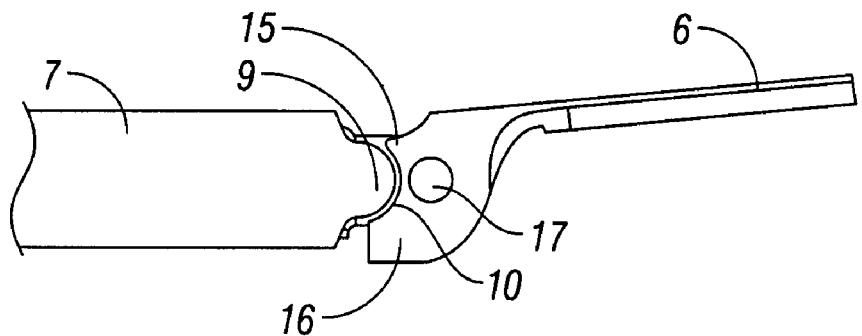
Figure 10:
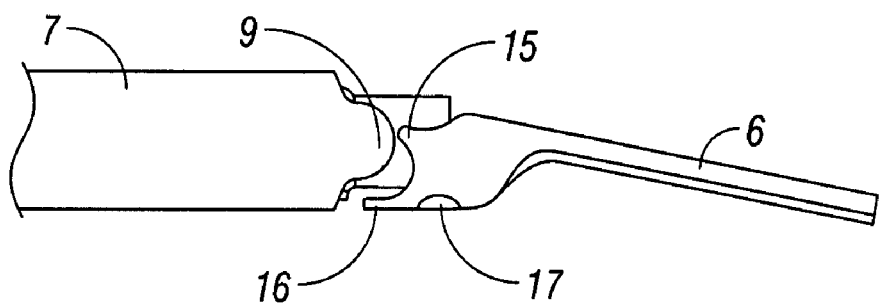
Figure 11:
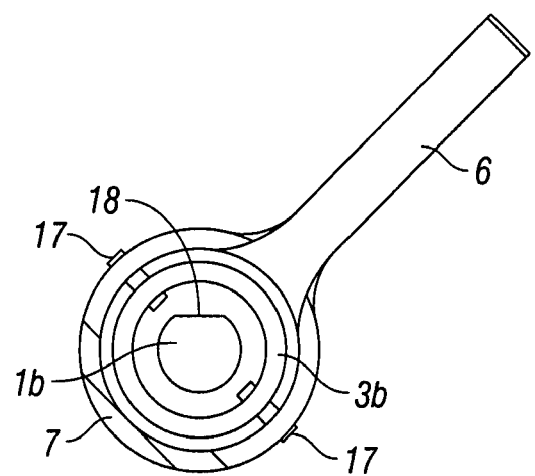
Figure 12:
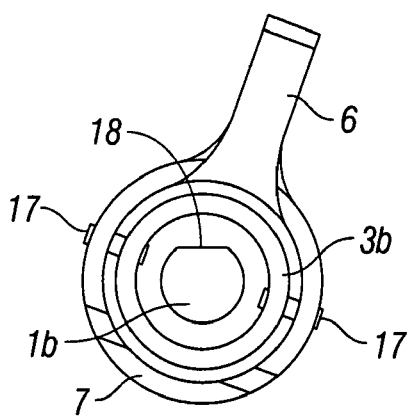
Figure 13:
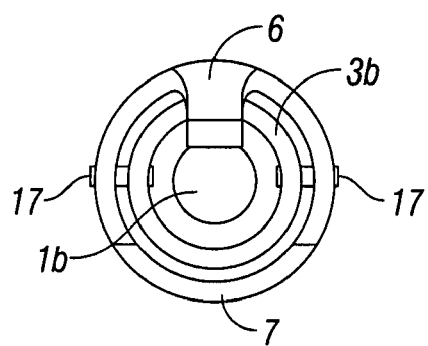
Figure 14:
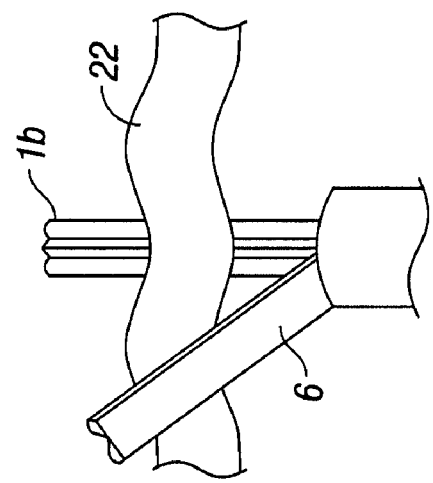
Figure 15:
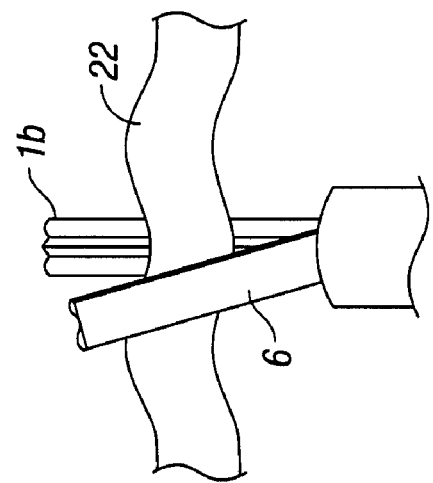
Figure 16:
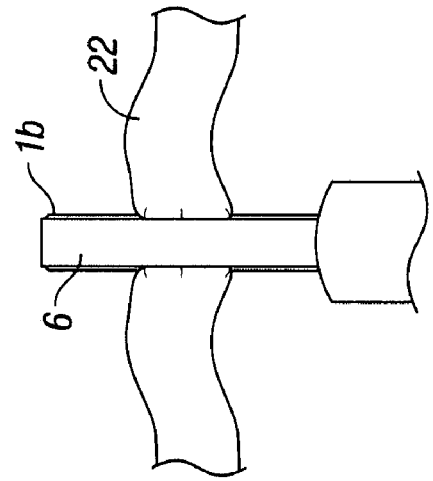

FIGS. 8 to 10 each show a distal end of the tool of FIG. 1, with the waveguide omitted and the jaw member being in an open disposition, an intermediate disposition and a closed disposition respectively;

FIGS 11 to 13 each show an end-on view of a distal end of the tool of FIG 1, the jaw member being in an open disposition, an intermediate disposition and a closed disposition respectively;

FIG. 14 shows a schematic perspective view of a distal end of the tool of FIG. 1 in an open disposition, prepatory to its use on a section of tissue;

FIG. 15 shows the distal end of the tool of FIG. 14 in an intermediate disposition, the jaws beginning to contact the section of tissue; and FIG. 16 shows the distal end of the tool of FIG. 14 in a closed disposition, gripping the section of tissue.

Referring now to the drawings and to FIG. 1 in particular, a surgical tool, in this case an ultrasonic surgical haemostatic tool, comprises an elongate waveguide 1 for ultrasonic vibrations (torsional mode ultrasonic vibrations are preferred, although longitudinal mode ultrasonic vibrations may also be utilised). The waveguide 1 defines a longitudinal axis of the tool, as shown by dotted line 2-2. A proximal end 1a of the waveguide 1 is mounted to an ultrasonic vibration generator (not shown).

The waveguide 1 is disposed coaxially within an elongate carrier tube 3, which is mounted at its proximal end to a cylindrical turning element 4. The carrier tube 3 and the turning element 4 are rotatable as a unit about the longitudinal axis 2, in the sense of arrows 5. The turning element 4 is acted on by a trigger mechanism or other manual operating means, as detailed below.

A jaw member 6 is mounted pivotably to a distal end 3b of the carrier tube 3.

A plurality of spacers (not shown) may be provided between the waveguide 1 and an inner wall of the carrier tube 3, insulating the carrier tube 3 from ultrasonic vibrations transmitted by the waveguide 1 and maintaining their relative disposition.

An outer tube 7 is disposed coaxially around the carrier tube 3 and the waveguide 1. The outer tube 7 is mounted at its proximal end to a mounting block 8, which is mounted non-rotatably to a handset of the tool (not shown in this Figure). At its distal end, the outer tube 7 is provided with a guide lobe 9, which bears on a rearward facing contact surface 10 of the jaw member 6. The turning element 4 and the mounting block 8 are biased apart, for example with a spring, other resilient device, or cam means such that the guide lobe 9 and the contact surface 10 remain co-operatingly in contact one with another.

When the carrier tube 3 is rotated, the contact surface 10 of the jaw member 6 mounted thereto moves across the guide lobe 9 of the stationary outer tube 7, thereby causing a pivoting movement of the jaw member 6 away from or towards contact with the distal end 16 of the waveguide 1, as detailed below.

The outer tube 7 also acts as a protective sheath for the greater part of the rotatable carrier tube 3 and the waveguide 1, for example protecting them from body fluids as far as possible. In a preferred embodiment of the tool, the carrier tube 3 and the outer tube 7 are detachable from the handset of the tool. The carrier tube 3 and the jaw member 6 that it carries may then be withdrawn in a distal direction from the outer tube 7, so that each may be cleaned and sterilised separately before re-use, or alternatively so that either or both may be disposed of and replaced with a fresh equivalent.

Figure 2:
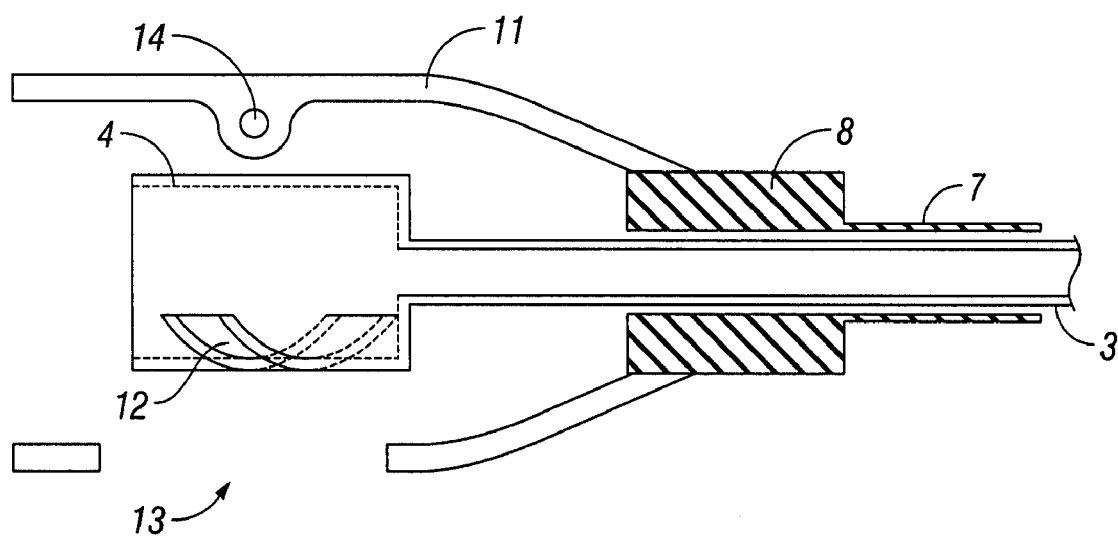
FIG. 2 is a scrap cross-sectional view of a part of the handset of the tool of FIG. 1 including a turning element.

FIG. 2 shows a part of the handset of the tool, together with proximal portions of the outer tube 7 and the carrier tube 3. The mounting block 8 is mounted, permanently or removably, to a handset casing 11. In this particular embodiment of the tool, the turning element 4 is provided with a part helical slot 12 in its cylindrical wall, which is adapted to receive a driving stud (not shown) mounted to a trigger mechanism (not shown) which extends out of the casing 11 through an aperture 13 provided therefor. The trigger mechanism may optionally be mounted to a pivot mounting 14 on the casing 11, as shown, or to a pivot mounting disposed adjacent the aperture 13. Pivoting movement of the trigger mechanism, which is configured to be grasped by a hand of a user, moves the driving stud in a generally longitudinal direction. As the driving stud is constrained to move within the part helical slot 12, a forward motion of the stud causes the turning element 4, and hence the carrier tube 3, to rotate in an anticlockwise sense (viewed from a proximal end of the tool) and a rearward motion of the stud causes the turning element 4 and the carrier tube 3 to rotate in a clockwise sense.

Note: the ultrasonic vibration generator is conveniently mounted inside a detachable element of the casing 11; FIG. 2 shows the handset with that element detached, and the waveguide 1, mounted to the ultrasonic generator, thereby withdrawn from its operating disposition disposed coaxially within the carrier tube 3.

The principle of operation of the jaw mechanism at the distal end of the tool is shown in FIGS. 3 to 6. The guide lobe 9 of the stationary outer tube 7 bears on the rearward facing contact surface 10 of the jaw member 6, which is bounded by two protrusions 15, 16 separated by an angle of no more than 180°, and preferably substantially less (see below). As described above, the jaw member 6 is pivotably mounted to a distal end 3b of the rotatable carrier tube 3 (not shown in these Figures for clarity) at a pivot point 17. When the carrier tube 3 rotates, the contact surface 10 moves across the corresponding surface of the guide lobe 9. When the carrier tube 3 rotates in a clockwise sense, protrusion 15 bears on the lobe 9, causing the jaw member 6 to pivot about pivot point 17 towards a closed disposition. When the carrier tube 3 rotates in an anticlockwise sense, protrusion 16 bears on the lobe 9, pivoting the jaw member away from the longitudinal axis 2 of the tool and the waveguide 1 (not shown in these figures), into a more open disposition.

For the configuration of jaw member 6 shown, when point C on the contact surface 10 is adjacent point A on the lobe 9, the jaw is closed; when point B on the contact surface 10 is adjacent point A, the jaw is partially open, at an angle of about 22.5° to the longitudinal axis 2; and when point D is adjacent point A, the jaw is fully open, at an angle of about 45°.

As can be seen, the degree of curvature of the contact surface 10 and the separation of the protrusions 15, 16 substantially dictate the change in angular disposition of the jaw member 6 and its rate of change produced by any given rotational movement of the carrier tube 3. It may, for example, be convenient for a rotation of the carrier tube 3 through as little as 20° to produce a jaw member 6 movement between a closed and a fully open disposition. The preferred degree of rotation is through an angle of between 25° and 35°.

Figure 5:
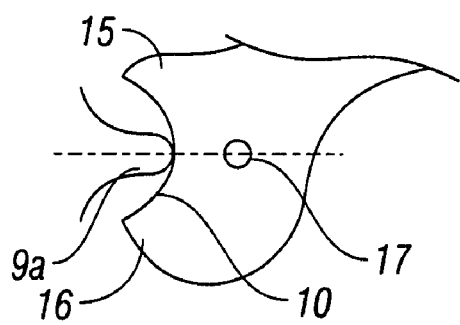
FIG. 5 is a scrap view of a possible contact area between the outer tube and the jaw member of the jaw mechanism of FIG. 3.
Figure 6:
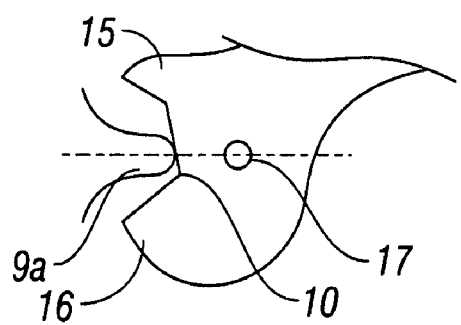
FIG. 6 is a scrap view of a further possible contact area between the outer tube and the jaw member.

The configuration of lobe 9 and contact surface 10 shown in FIG. 3, where each has a generally circular profile, gives a substantially linear correlation between rotation and jaw movement. However, other profiles may be preferred for specific purposes. For example, in FIG. 5 the contact surface 10 has a parabolic curve, which gives a longer dwell time at an intermediate point in the coming together of the jaws. Note: FIGS. 5 and 6 show an alternative profile of guide lobe 9a, more sharply curved than that of FIG. 3, which is preferred for co-operation with more complex profiles of the contact surface 10.

FIG. 6 shows a preferred arrangement in which the protrusion 16 contacts the lobe 9a with the jaw member 6 open at about 45° to the longitudinal axis 2. As the carrier tube 3 rotates, drawing the contact surface 10 across the lobe 9a, the contact surface 10 is so curved that the jaw member 6 closes only very slowly during a first phase, followed by a final sharp closure caused by protrusion 15 bearing on lobe 9a. In the first phase, the jaw member 6 may be used to press a section of tissue lightly towards the ultrasonically-vibrating waveguide 1, which leads to comparatively gradual coagulation of the tissue, followed by rapid cutting of the tissue during the final closure of the jaws.

The advantage of this arrangement is that a single smooth manual operation of the trigger mechanism produces variable selected degrees of pressure on the workpiece; the surgeon does not have to concern himself with differential pressure on the trigger mechanism at successive states of the operation.

Figure 7:
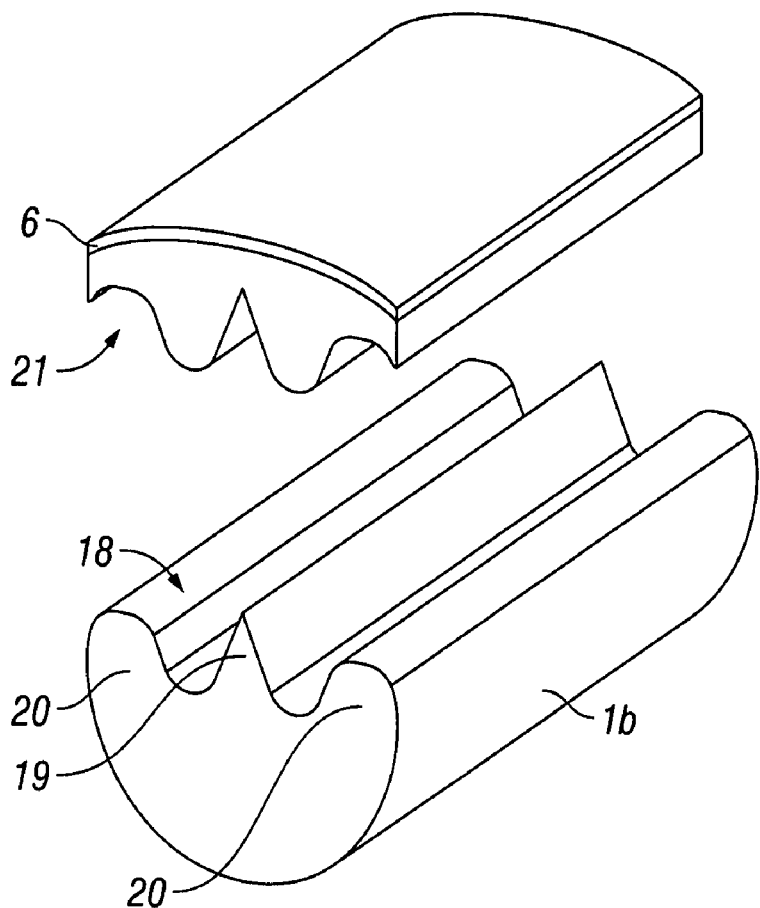
FIG. 7 is a scrap perspective view of one possible jaw member arrangement of a cutting and coagulating tool.

FIG. 7 shows a configuration of jaw member 6 and distal end 1b of the waveguide 1 which is particularly suitable for use in conjunction with the jaw mechanism of the present invention in an ultrasonic cutting and coagulating tool. (Other configurations may also be employed, some of which are described in British Patent No. 2333709B). The distal end 1b is configured to be an ultrasonically vibratable anvil, with an operating surface 18 having a profile which comprises a central acutely-angled cutting element 19, flanked by two relatively rounded coagulating elements 20. The jaw member 6 has a holding surface 21 which has a complementary shape to that of the operating surface 18.

Operation of the jaw mechanism as described above brings the holding surface 21 down towards the operating surface 18, such that soft tissue, for example a blood vessel, may be held between the surfaces 18, 21.

Torsional ultrasonic vibrations transmitted along the waveguide 1 to its distal end 1b cause the rounded elements 20 to act against a corresponding portion of the holding surface 21, coagulating the tissue and sealing the blood vessel, while the central element 19 acts against the corresponding portion of the holding surface 21 to sever the blood vessel.

As described above, the arrangements shown in FIGS. 3 to 6 enable the two surfaces 18, 21 to be brought together in a controlled manner, avoiding damaging the blood vessel before it can be sealed. The arrangement of FIG. 6 shows how the jaw mechanism can be configured so as to produce a comparatively long period of coagulation as the surfaces 18, 21 are brought gradually towards one another, and a short sharp period of cutting as the surfaces finally come into contact.

FIGS. 8 to 10 show the sequence of operation of the jaw mechanism in more detail, with the outer tube 7 and its guide lobe 9 stationary during this sequence.

In FIG. 8, the jaw member 6 is in its fully open disposition, and the protrusion 16 is bearing on the guide lobe 9 of the guide tube 7. The carrier tube 3b is then rotated clockwise (viewed from a proximal end of the tool). The contact surface 10 of the jaw member 6 thus slides across an opposing surface of the guide lobe 9, and the jaw member 6 pivots until the disposition of FIG. 9 is reached. The portion of the contact surface 10 between the protrusions 15, 16 is bearing on the guide lobe 9, and the jaw member 6 is in an intermediate position. Further clockwise rotation of the carrier tube 3b brings the protrusion 15 into operative contact with the guide lobe 9, and thus pivots the jaw member 6 further about the pivot point 17 until the disposition of FIG. 10 is reached, with the jaw member 6 fully closed.

Anticlockwise rotation of the carrier tube 3 reverses this sequence.

Note: for clarity of illustration, a small gap is shown between the contact surface 10 of the jaw member and the guide lobe 9. As indicated above, it is important that they remain in contact, and the carrier tube 3 and outer tube 7 are biased relative to one another, so that the contact surface 10 is urged into contact with the guide lobe 9 at all stages of the above operation.

It will be apparent from the above that while the jaw member 6 is performing a simple pivoting motion about its pivot point 17, the carrier tube 3 to which it is pivoted is rotating about its longitudinal axis 2. Hence the tip of the jaw member moves through a three-dimensional path relative to its surroundings.

FIGS. 11 to 13 show the operation of the jaw mechanism when viewed from a distal end of the tool, and correspond generally to FIGS. 8 to 10 respectively. In FIG. 11, the jaw member 6 is in a fully open disposition, and the carrier tube 3b is rotated filly clockwise (from a distal point of view). The majority of the outer tube 7, including the guide lobe 9, is concealed in this view. In FIG. 12, the carrier tube 3b has rotated anti-clockwise (as seen) relative to the outer tube 7 and the waveguide 1b, and has thus moved the jaw member 6 anticlockwise as well as closing it towards the waveguide 1b. In FIG. 12, the carrier tube 3b has rotated fully anticlockwise (as seen), closing the jaw member 6 into contact with the waveguide 16 and rotating it into alignment with the operating surface 18 thereof (here shown as a plane surface for simplicity). Selection of the appropriate configurations of the guide lobe 9 and the contact surface 10 can clearly control the relative magnitude of the closing and turning movements of the jaw member 6 and hence the exact track that it traces. The beneficial consequences of these movements of the jaw member, from a surgeon's point of view (more precisely, from a surgeon's point of view through an endoscope), may be seen in FIGS. 14 to 16. In these figures, the details of the jaw mechanism are omitted for clarity.

In FIG. 14, the jaw member 6 is fully open and rotated to the left, as viewed from the proximal end of the tool. The distal end 1b of the waveguide is thus clearly visible and can be accurately positioned beneath a piece of tissue, here a blood vessel 22, to be severed. In FIG. 15, the jaw member 6 is partially closed and is beginning to press the blood vessel 22 against the ultrasonically-vibrating waveguide 1b. Between FIGS. 15 and 16, the jaw member 6 continues to press the blood vessel 22 against the waveguide 1b, which ultrasonically coagulates it, until in the fully closed position of FIG. 16, the waveguide 1b and the jaw member 6 act to sever the blood vessel 22, as described above. The severed and sealed blood vessel is released by reversing this sequence. As can be seen, the surgeon's view of the portion of the blood vessel 22 to be coagulated and cut is only obscured by the jaw member 6 in the latter stags of its closure, once it has begun to grip the blood vessel. This allows for easier and more accurate positioning of the tool, and for last-moment minor positioning adjustments if necessary.

The tool described above thus allows a surgeon superior control over its use and a superior view of what is being done. It is also relatively simple to produce, compared to previous surgical tools of this type, and it is straightforward to disassemble the parts which come into contact with the body for cleaning or replacement.

The invention claimed is:

1. A surgical tool capable of transmitting torsional ultrasonic vibrations, said surgical tool comprising a longitudinally extending guide defining a longitudinal axis of said tool, a first jaw member at a distal end thereof having an operating surface with a profile comprising an angled cutting element and a coagulating element, a longitudinally extending carrier rotatable about said guide, a second jaw member mounted pivotably to a distal end of said carrier, said second jaw member having a surface which has complementary shape to that of the operating surface of the first jaw member, and outer shroud including operating means for actuating said second jaw member wherein rotation of said carrier acts on the operating means to cause pivoting of said second jaw member into and out of operative relationship with said first jaw member, wherein the second jaw member pivots about a first axis substantially simultaneously with rotation of the first axis about a second axis substantially orthogonal to the first axis.

2. A tool as claimed in claim 1, wherein the surgical tool is an ultrasonic surgical tool, and the elongate guide is a waveguide for propagating one of torsional ultrasonic vibrations and longitudinal ultrasonic vibrations, operatively connected at a proximal end to an ultrasonic vibration generator.

3. A tool as claimed in claim 2, wherein the operating surface of the first jaw member constitutes an ultrasonically vibratable cutter and/or coagulator, and the proximally facing surface of the second jaw member is adapted to hold tissue to be treated against said cutter and/or coagulator.

4. A tool as claimed in claim 1 wherein said carrier is a carrier tube, comprising a tubular member concentrically surrounding said guide.

5. A tool as claimed in claim 4, wherein the carrier tube is rotatable within a tubular space defined by an inner wall of the outer shroud and an outer surface of the inner guide member.

6. A tool as claimed in claim 1, wherein the shroud is mounted non-rotatably to a handset of the tool.

7. A tool as claimed in claim 6, wherein the shroud is detachably mounted to said handset, as is the carrier.

8. A tool as claimed in claim 1, wherein the operating means comprises a guide lobe extending forwardly from a distal end of the shroud means and disposed to bear on an opposing surface of the second jaw member.

9. A tool as claimed in claim 8, wherein the operating means comprises two cam lobes extending proximally towards the distal end of the guide.

10. A tool as claimed in claim 8, wherein said proximally facing surface of the second jaw member comprises an intermediate curved zone disposed between two protrusions, so disposed that by relative rotational movement the action of one said protrusion on a guide lobe of the operating means acts to pivot the second jaw member into operative relationship with the operating surface of the first jaw member, and the action of the other said protrusion on the guide lobe acts to pivot the second jaw member away from said operative relationship.

11. A tool as claimed in claim 10, wherein the protrusions and the curved zone therebetween cooperate with the guide lobe to move the second jaw member between open and closed dispositions by a rotational movement of the carrier to which said second jaw member is mounted of between 20 and 60 degrees.

12. A tool as claimed in claim 11, wherein the second jaw member is mounted between 25 and 45 degrees.

13. A tool as claimed in claim 10, wherein the curved zone is so shaped that the second jaw member is caused to pivot comparatively slowly over a part of its travel and comparatively rapidly over another part of its travel.

14. A tool as claimed in claim 13, wherein the comparatively slow part of the travel of the second jaw member defines a coagulation step, and the comparatively rapid part of said travel defines a cutting step.

15. A tool as claimed in claim 8, wherein the operating means is provided with more than one guide lobe, preferably an odd number thereof.

16. A tool as claimed in claim 15, wherein the second jaw member has only a single protrusion, guided by two said lobes and a curved interlobal zone therebetween.

17. A tool as claimed in claim 1, wherein the carrier is operatively connected to a manually operable means for controlling, which control means includes means to ensure substantially continuous contact between the guide lobe or lobes and the proximal face of the second jaw member, whatever their rotational disposition.

18. A tool as claimed in claim 17, wherein the carrier being biased in a proximal direction by a resilient biasing means, said resilient biasing means being a spring or a member of resilient material, or cam adapted to urge the carrier means in a proximal direction.

19. A tool as claimed in claim 1, wherein the second axis is substantially orthogonal to the first axis.

20. A tool as claimed in claim 1, wherein the second axis is parallel or coincident with the longitudinal axis.

21. A tool as claimed in claim 1, wherein the second jaw member moves along a three dimensional path relative to the first jaw member.

22. A surgical tool capable of transmitting torsional ultrasonic vibrations, said surgical tool comprising a longitudinally extending first guide member having a first jaw member at a distal end thereof having an operating surface with a profile comprising an angled cutting element and a coagulating element, a second jaw member movable into and out of operative relationship with the first jaw member and a carrier, the second jaw member having a surface which has a complementary shape to that of the operating surface of the first jaw member, and operating means for actuating the second jaw member so adapted that the second jaw member pivots about a first axis substantially simultaneously with rotation of the first axis about a second axis substantially orthogonal to the first axis and follows a three dimensional path relative to the first jaw member when so moved.

23. A tool as claimed in claim 22, wherein the second axis is substantially orthogonal to the first axis.

24. A tool as claimed in claim 22, wherein the longitudinally extending first guide member defines a longitudinal axis and the second axis is parallel or coincident with the longitudinal axis.

25. A method for severing and coagulating tissue using torsional ultrasonic vibrations comprising:
    providing a waveguide having a first jaw member at a distal end thereof and capable of transmitting torsional ultrasonic vibrations to the distal end thereof, the first jaw member having an operating surface with a profile comprising an angled cutting element and a coagulating element;
    providing a second jaw member having a surface which has a complementary shape to that of the operating surface of the first jaw member;
    moving the second jaw member into and out of operative relationship with the first jaw member comprising pivoting the second jaw member about a first axis and substantially simultaneously rotating the first axis about a second axis disposed at an angle relative to the first axis;
    clamping tissue between first and second jaw members of an ultrasonic tool capable of transmitting torsional ultrasonic vibrations to the distal end thereof;
    causing torsional ultrasonic vibrations to be transmitted to the first jaw member; and
    applying pressure to press the tissue between the first and second jaw members for ultrasonically severing and coagulating the tissue.

26. A method as claimed in claim 25, wherein the first jaw member constitutes ultrasonically vibratable cutter and/or coagulator means, and the second jaw member is adapted to bold the tissue against said cutting and/or coagulating means.

27. A method as claimed in claim 25, wherein the second axis is substantially orthogonal to the first axis.

28. A method as claimed in claim 25, wherein the second axis is parallel or coincident with the longitudinal axis.

29. A method as claimed in claim 25, wherein the second jaw member moves along a three dimensional path relative to the first jaw member.

* * * * *